United States Patent
Jiang et al.

(10) Patent No.: US 10,959,928 B2
(45) Date of Patent: Mar. 30, 2021

(54) FOAMABLE PERSONAL CARE COMPOSITION AND THE USE THEREOF

(71) Applicant: Henkel AG & Co. KGaA, Duesseldorf (DE)

(72) Inventors: Yihua Jiang, Shanghai (CN); Xiaowei Chang, Shanghai (CN); Bruce Cox, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/565,169

(22) PCT Filed: Apr. 22, 2015

(86) PCT No.: PCT/CN2015/077164
§ 371 (c)(1),
(2) Date: Oct. 9, 2017

(87) PCT Pub. No.: WO2016/169000
PCT Pub. Date: Oct. 27, 2016

(65) Prior Publication Data
US 2018/0092818 A1    Apr. 5, 2018

(51) Int. Cl.
| | | |
|---|---|---|
| *A61K 8/365* | (2006.01) | |
| *A61Q 5/02* | (2006.01) | |
| *A61Q 5/12* | (2006.01) | |
| *A61K 8/73* | (2006.01) | |
| *A61K 8/04* | (2006.01) | |
| *A61K 8/19* | (2006.01) | |
| *A61K 8/44* | (2006.01) | |
| *A61Q 19/10* | (2006.01) | |

(52) U.S. Cl.
CPC .............. *A61K 8/365* (2013.01); *A61K 8/046* (2013.01); *A61K 8/19* (2013.01); *A61K 8/442* (2013.01); *A61K 8/731* (2013.01); *A61Q 5/02* (2013.01); *A61Q 5/12* (2013.01); *A61Q 19/10* (2013.01); *A61K 2800/222* (2013.01); *A61K 2800/48* (2013.01)

(58) Field of Classification Search
None
See application file for complete search history.

(56) References Cited

U.S. PATENT DOCUMENTS

| | | |
|---|---|---|
| 5,804,546 A | 9/1998 | Hall |
| 6,177,092 B1 | 1/2001 | Lentini et al. |
| 2004/0023825 A1 | 2/2004 | Davies et al. |
| 2004/0042988 A1* | 3/2004 | Raney ..................... A61Q 5/00 424/70.1 |
| 2005/0042261 A1* | 2/2005 | Hasenoehrl .......... A61K 8/0208 424/443 |
| 2006/0147399 A1 | 7/2006 | McNamara et al. |
| 2006/0229226 A1 | 10/2006 | Giniger et al. |
| 2009/0010855 A1* | 1/2009 | Lepilleur ............... A61K 8/737 424/47 |
| 2011/0256085 A1* | 10/2011 | Talingting Pabalan ..................... A61K 8/042 424/70.13 |
| 2013/0244976 A1 | 9/2013 | Inamoto |
| 2014/0260466 A1* | 9/2014 | Rehage ................... C05F 11/00 71/23 |

FOREIGN PATENT DOCUMENTS

| | | |
|---|---|---|
| CN | 1119935 A | 4/1996 |
| DE | 10015149 A1 | 12/2001 |
| DE | 102005007293 A1 | 8/2006 |
| GB | 758020 A | 9/1956 |
| JP | S63135317 A | 6/1988 |
| JP | H0959674 A | 3/1997 |
| WO | 9014070 A1 | 11/1990 |
| WO | WO-9924492 A1 * | 5/1999 .............. C08L 23/08 |
| WO | 0027356 A1 | 5/2000 |

OTHER PUBLICATIONS

EPO, International Search Report and Written Opinion issued in International Application No. PCT/CN2015/077164, dated Jan. 7, 2016.
European Patent Office, Extended European Search Report under Rule 62 EPC, for European Patent Application No. 15889489.9 dated Dec. 12, 2018.

* cited by examiner

Primary Examiner — David J Blanchard
Assistant Examiner — Sarah J Chickos
(74) Attorney, Agent, or Firm — Lorenz & Kopf, LLP

(57) ABSTRACT

The present disclosure relates to a foamable personal care composition, a personal care kit of parts, and uses thereof. In particular, the present disclosure relates to a foamable personal care composition and a personal care kit of parts used in skin or hair treatment.

13 Claims, 3 Drawing Sheets

US 10,959,928 B2

FOAMABLE PERSONAL CARE COMPOSITION AND THE USE THEREOF

CROSS-REFERENCE TO RELATED APPLICATION

This application is a U.S. National-Stage entry under 35 U.S.C. § 371 based on International Application No. PCT/CN2015/077164, filed Apr. 22, 2015 which was published under PCT Article 21(2), which is hereby incorporated in their entirety by reference.

TECHNICAL FIELD

The present disclosure relates to a foamable personal care composition, a personal care kit of parts, and uses thereof. In particular, the present disclosure relates to a foamable personal care composition and a personal care kit of parts used in skin or hair treatment.

BACKGROUND

Nowadays, more and more people pay attention on the health of scalp and hair. It is believed that a healthy scalp will give a good condition for hair growth. Although there are many scalp and hair care products on the market, the forms of the products are commonplace and limited to lotion, cream, gel, etc. which are lacking aesthetic elements that are appealing to consumers.

Foaming action is primarily desirable at the time such product is applied to and during use on the skin or the hair. A formable hair care product may have advantages of creating a significant amount of foams and bubbles in short term and thus attract consumer's attention and interests. Among them, foaming systems producing carbon dioxide, essentially including of an acid and a carbonate or bicarbonate have been developed since they are self-forming and thus there is no need to use propellants which are not safe and environment-friendly.

WO 200027356 A1 discloses a cosmetic or pharmaceutical self-foaming system for application to the skin or hair, comprising an acid component and an alkali metal bicarbonate component contained in a cosmetically and/or pharmaceutically acceptable carrier.

JP 563135317 A discloses a detergent containing a surface active agent or soap as an active ingredient for the detergent is blended with a carbonic acid gas generating substance, especially sodium carbonate or sodium bicarbonate; an inorganic acid, organic acid or an acidic salt thereof; and an emollient agent, preferably polypeptide, keratin, sugar ester or olive oil. WO 90/14070 A discloses foaming hair conditioning and care compositions containing organic acid, carbonate and caring agents.

GB 758020 A discloses a formed detergent composition including in forming a concentrated aqueous solution of a synthetic detergent having foaming characteristics, the said solution containing free acid and adding thereto a powdered carbonate or bicarbonate which, in the present of water, will liberate carbon dioxide on contact with the said acid.

There is still a need to develop an improved formable personal care composition which produces dense and homogeneous foams with a significant amount and stability over time for skin or hair treatment which allows a massage step taking a longer period of time.

BRIEF SUMMARY

One aspect of the present disclosure is a foamable personal care composition, comprising components:

(a) from about 1 to about 8% by weight of a cosmetically acceptable acidic component,
(b) from about 1 to about 8% by weight of an alkali metal carbonate or bicarbonate component,
(c) a carrier component, comprising:
(c1) from about 0.5 to about 1.8% by weight of a cellulose thickener having a Brookfield viscosity of from about 800 to about 50,000 mPa·s, measured by a Brookfield RVDV II+ viscometer using spindles No. 2 to 6 at a rotation speed of 20 $min^{-1}$ in 1% by weight aqueous solution of the cellulose thickener at 20° C.,
(c2) from about 1 to about 8% by weight of a surfactant selected from the group including of amphocarboxylate salt having from 2 to 12 carbon atoms in the carboxylate group, amphodicarboxylate salt having from 2 to 12 carbon atoms in the carboxylate group, and combination thereof, and
(c3) from about 80 to about 95% by weight of water,
in which the weight ratios of the components are based on the total amount of all components of the foamable personal care composition.

A further aspect of the present disclosure is a personal care kit of parts, comprising the foamable personal care composition according to the present disclosure, wherein the cosmetically acceptable acidic component and the alkali metal carbonate or bicarbonate component are separated in different parts and do not contact with each other.

Another aspect is a foamed product produced by mixing the components of the foamable personal care composition according to the present disclosure or the kit of parts according to the present disclosure.

Yet another aspect is the use of the foamable personal care composition according to the present disclosure, the kit of parts according to the present disclosure, or the foamed product according to the present disclosure in a skin or hair care treatment.

Yet another aspect is a method of conditioning skin or hair, comprising applying the foamed product according to the present disclosure.

Other features and aspects of the subject matter are set forth in greater detail below.

BRIEF DESCRIPTION OF THE DRAWINGS

The present disclosure will hereinafter be described in conjunction with the following drawing figures, wherein like numerals denote like elements, and.

DETAILED DESCRIPTION

Figure 1:
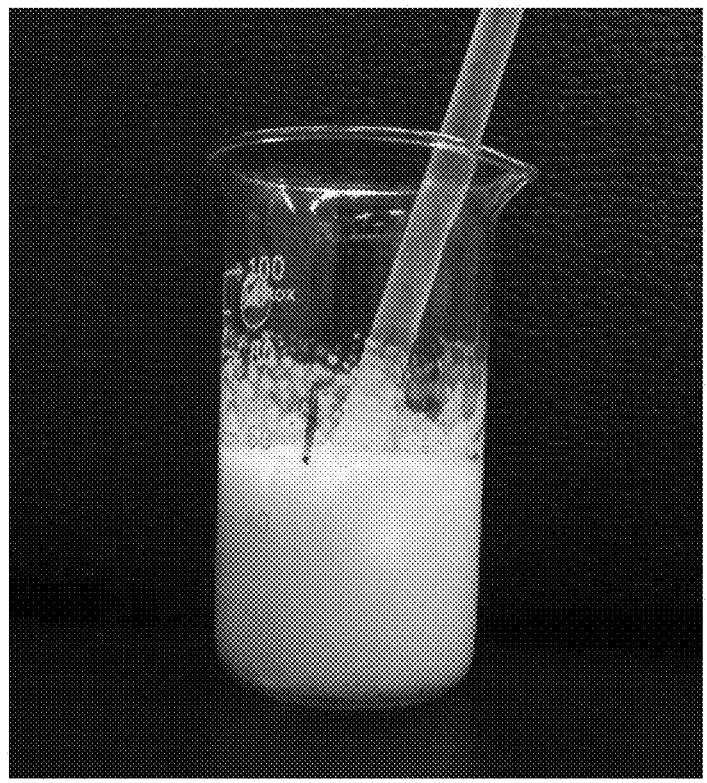
FIGS. 1 and 2 illustrate the initial foams of Comparative Examples 7, 8 and Inventive Example 3.

The following detailed description is merely exemplary in nature and is not intended to limit the disclosure or the application and uses of the subject matter as described herein. Furthermore, there is no intention to be bound by any theory presented in the preceding background or the following detailed description.

It is to be understood by one of ordinary skill in the art that the present discussion is a description of exemplary embodiments only, and is not intended as limiting the broader aspects of the present disclosure.

"Cosmetically acceptable" refers to components or ingredients typically used in foamable personal care compositions, and is intended to underscore that materials that are toxic when present in the amounts typically found in foamable personal care compositions are not contemplated as part of the present disclosure.

"Personal care" relates to compositions to be topically applied to a person (including mouth, ear, and nasal cavities, but not ingested). Examples of foamable personal care compositions include skin care products (e.g., facial cream, moisturizers, leave on and rinse off lotions, sunscreens, foundation, mascara, eye-liner, lipstick, cleansers, and the like) and hair care products (including shampoos, leave on and rinse off conditioners, styling gels and hairsprays). Preferably, the foamable personal care composition according to the present disclosure is a shampoo, a rinse-off conditioner, a leave-in conditioner, or a body wash.

In one aspect, the present disclosure is generally directed to a foamable personal care composition, comprising components:
(a) from about 1 to about 8% by weight of a cosmetically acceptable acidic component,
(b) from about 1 to about 8% by weight of an alkali metal carbonate or bicarbonate component,
(c) a carrier component, comprising:
(c1) from about 0.5 to about 1.8% by weight of a cellulose thickener having a Brookfield viscosity of from about 800 to about 50,000 mPa·s, measured by a Brookfield RVDV II+ viscometer using spindles No. 2 to 6 at a rotation speed of 20 $min^{-1}$ in 1% by weight aqueous solution of the cellulose thickener at 20° C.,
(c2) from about 1 to about 8% by weight of a surfactant selected from the group including of amphocarboxylate salt having from 2 to 12 carbon atoms in the carboxylate group, amphodicarboxylate salt having from 2 to 12 carbon atoms in the carboxylate group, and combination thereof, and
(c3) from about 80 to about 95% by weight of water,
in which the weight ratios of the components are based on the total amount of all components of the foamable personal care composition.

Component (a)

There is no particular limitation to the cosmetically acceptable acidic component in the present disclosure as long as the component is safe for use and can react with alkali metal carbonate or bicarbonate component and release a mass of carbon dioxide which will in turn produce long-lasting foams.

In one embodiment of the present disclosure, the cosmetically acceptable acidic component comprising or including of a cosmetically acceptable acidic compound selected from the group including of a cosmetically acceptable organic acid, acidic salt thereof, a cosmetically acceptable inorganic acid, acidic salt thereof, and combination thereof.

Preferably, the cosmetically acceptable organic acid is selected from the group including of citric acid, ascorbic acid, tartaric acid, lactic acid, salicylic acid, gluconic acid, malic acid, fumaric acid, and combination thereof.

Preferably, the acidic salt of the cosmetically acceptable organic acid is selected from the group including of potassium tartrate, potassium bitartrate, calcium lactate, and combination thereof.

Preferably, the cosmetically acceptable inorganic acid according to the present disclosure is selected from the group including of pyrophosphoric acid, phosphoric acid, sulfuric acid, and combination thereof.

Preferably, the acidic salt of the cosmetically acceptable inorganic acid is selected from the group including of calcium sulfate, calcium phosphate, sodium aluminum phosphate, sodium aluminum sulfate, monosodium phosphate, disodium pyrophosphate, and combination thereof.

According to the present disclosure, the cosmetically acceptable acidic component can be singly present or combined with the carrier component. The physical form of the cosmetically acceptable acidic component may be in solid or solution. If it is in solid, a fine powder of the component, preferably have an average particle size less than about 100 microns will be more preferred to be used in the present disclosure. If it is in solution, the component may singly present, or the acids and/or acidic salts may also dissolved in the carrier component which is inert to the acids and/or acidic salts and further contains water and/or other solvents. In either instance, the pH value of will be in the range of from about 1 to about 4, more preferably from about 2 to about 3.

In one preferred embodiment of the present disclosure, the cosmetically acceptable acidic component is citric acid either in the form of solid or aqueous solution.

Preferably, the cosmetically acceptable acidic component is present in an amount of from about 2 to about 6% by weight, preferably from about 3 to about 5% by weight of the total amount of the foamable personal care composition.

Component (b)

In the present disclosure, the cosmetically acceptable alkali metal carbonate or bicarbonate includes but is not limited to sodium or potassium carbonate or sodium or potassium bicarbonate. In one embodiment of the present disclosure, the cosmetically acceptable alkali metal carbonate or bicarbonate is sodium bicarbonate.

According to the present disclosure, the cosmetically acceptable alkali metal carbonate or bicarbonate component can be singly present or combined with the carrier component. The physical form of the cosmetically acceptable acidic component may be in solid or solution. If it is in solid, a fine powder of the component, preferably have an average particle size less than about 100 microns will be more preferred to be used in the present disclosure. If it is in solution, the component may singly present as e.g. an aqueous solution, or the alkali metal carbonate or bicarbonate may also dissolved in the carrier component which is inert to the alkali metal carbonate or bicarbonate and further contains water and/or other solvents. In either instance, the pH value of will be in the range of from about 10 to about 13, more preferably from about 11 to about 12.

Preferably, the alkali metal carbonate or bicarbonate is present in an amount of from about 2 to about 6% by weight, preferably from about 3 to about 5% by weight of the total amount of the foamable personal care composition.

Preferably, the amount of the alkali metal carbonate or bicarbonate is equal or slightly excessive or slightly insufficient to that of the cosmetically acceptable acidic component. The pH value of the product is preferably from about 5 to about 9, and more preferably from about 6 to about 8 so that the product will not irritate the skin or scalp during application and subsequent treatment.

Component (c)

The foamable personal care composition further contains a carrier component, comprising (c1) from about 0.5 to about 1.8% by weight of a cellulose thickener having a Brookfield viscosity of from about 800 to about 50,000 mPa·s, measured by a Brookfield RVDV II+ viscometer using spindles No. 2 to 6 at a rotation speed of 20 $min^{-1}$ in 1% by weight aqueous solution of the cellulose thickener at 20° C., (c2) from about 1 to about 8% by weight of a surfactant selected from the group including of amphocarboxylate salt having from 2 to 12 carbon atoms in the carboxylate group, amphodicarboxylate salt having from 2 to 12 carbon atoms in the carboxylate group, and combination thereof, and (c3) from about 80 to about 95% by weight of water, in which the weight ratios are based on the total amount of all components of the foamable personal care composition.

According to the present disclosure, the particular selection of thickener and surfactant contributes to a mass amount of dense foams having satisfactory stability over an extended period of for example 15 minutes. Both of the initial volume of foams created by the compositions and the volume after foaming 15 min (showing stability of the foam) are higher compared to the volume of composition before reaction, so that the foam mass would be attractive to the user and have a magic feel.

Preferably, the ratio of the initial volume of foam to the volume of the foamable personal care composition is larger than 5.0, preferably larger than 5.5, at 25° C. and atmospheric pressure.

Preferably, the ratio of the foam volume at 15 minutes after the foam reaches the highest foam volume to the volume of the foamable personal care composition is larger than 3.0, preferably no less than 3.2, at 25° C. and under atmospheric pressure.

The cellulose thickener suitable to be used in the present disclosure has a Brookfield viscosity of from about 800 to about 50,000 mPa·s, measured by a Brookfield RVDV II+ viscometer using spindles No. 2 to 6 at a rotation speed of 20 $min^{-1}$ in 1% by weight aqueous solution of the cellulose thickener at 20° C. Specifically, if other test conditions are not changed, spindle No. 2 can be used for the viscosity of from about 800 to about 2,000 mPa·s, spindle No. 3 can be used for the viscosity of from larger than 2,000 to 5,000 mPa·s, spindle No. 4 can be used for the viscosity of from larger than about 5,000 to about 10,000 mPa·s, spindle No. 5 can be used for the viscosity of from larger than about 10,000 to about 20,000 mPa·s, and spindle No. 6 can be used for the viscosity of from larger than about 20,000 to about 50,000 mPa·s.

The viscosity of the cellulose thickener may influence the performance of the foams. If the Brookfield viscosity of the cellulose thickener is lower than 800 mPa·s, the stability of foams will be deteriorated. In one embodiment of the present disclosure, the cellulose thickener has a Brookfield viscosity of from about 1,000 to about 20,000 mPa·s, preferably from about 1,000 to about 10,000 mPa·s.

In one embodiment, the cellulose thickener is selected from the group including of carboxymethyl cellulose, hydroxyethyl cellulose, hydroxyethyl ethylcellulose, hydroxypropyl methylcellulose, and combination thereof.

Preferably, the cellulose thickener is present in an amount of from about 0.7 to about 1.6% by weight, preferably from about 0.8 to about 1.5% by weight of the total amount of the foamable personal care composition.

Together with the cellulose thickener, the surfactant used in the present disclosure also contributes to the creation of dense and stable foams. In one embodiment, as a suitable surfactant, the amphocarboxylate salt having from 2 to 12 carbon atoms, preferably having from 2 to 8 carbon atoms in the carboxylate group is selected from the group including of cocoamphoacetate salt, cocoamphopropionate salt, stearoamphoacetate salt, capryloamphopropionate salt, and combination thereof. The amphodicarboxylate salt having from 2 to 12 carbon atoms, preferably having from 2 to 8 carbon atoms in the carboxylate group is preferably selected from the group including of cocoamphodiacetate salt, coco-amphodipropionate salt, capryloamphodiacetate salt, capryloamphodipropionate salt, tallamphodipropionate salt, lavroamphodiacetate salt, and combination thereof.

In one preferred embodiment, the surfactant is a cocoamphodiacetate salt, preferably disodium cocoamphodiacetate salt.

Preferably, the surfactant is present in an amount of from about 1.5 to about 6% by weight, preferably from about 2 to about 5% by weight of the total amount of the foamable personal care composition.

Additive components may also be contained in the composition and include but not be limited to cosmetically acceptable solvent, humectants, emollients, sunscreens, surfactants, emulsifiers, preservatives, rheology modifiers, colorants, dyes, preservatives, reducing agents, fragrances, tanning agents, depilatory agents, flavors, astringents, antiseptics, deodorants, antiperspirants, insect repellants, bleaches, lighteners, anti-dandruff agents, adhesives, polishes, strengtheners, fillers, barrier materials, and biocides.

Solvents are contained in the carrier component. In one embodiment of the present disclosure, the solvent is water, preferably deionized water. The cosmetically acceptable acidic component and/or the alkali metal carbonate or bicarbonate component may individually dissolved in the carrier component before use.

Examples of humectants include polyhydric alcohols, water soluble alkoxylated nonionic polymers, and mixtures thereof. Polyhydric alcohols useful herein include polyhdroxy alcohols aforementioned and glycerin, hexylene glycol, ethoxylated glucose, 1,2-hexane diol, dipropylene glycol, trehalose, diglycerin, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof. Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof. In one preferred embodiment, the foamable personal care composition further comprises sodium hyaluronate.

Examples of colorants include pigments which may be selected from metal oxide pigments, titanium dioxide, optionally surface-treated, zirconium oxide or cerium oxide, zinc oxide, iron oxide (black, yellow or red), chromium oxide, manganese violet, ultramarine blue, chromium hydrate and ferric blue, carbon black, pigments of barium, strontium, calcium or aluminum, cochineal carmine, mica coated with titanium or with bismuth oxychloride, titanium mica with iron oxides, titanium mica with, especially, ferric blue or chromium oxide, titanium mica with an organic pigment, nacreous pigments based on bismuth oxychloride, goniochromatic pigments, for example pigments with a multilayer interference structure, reflective pigments, for example particles with a silver-coated glass substrate, glass substrate coated with nickel/chromium/molybdenum alloy, glass substrate coated with brown iron oxide.

Examples of dyes include water-soluble dyes such as copper sulfate, iron sulfate, water-soluble sulfopolyesters, rhodamines, natural dyes, for instance carotene and beetroot juice, methylene blue, caramel, the disodium salt of tartrazine and the disodium salt of fuschin, and mixtures thereof.

Examples of preservatives include alcohols, aldehydes, methylchloroisothiazolinone and methylisothiazolinone, p-hydroxybenzoates, and in particular methylparaben, propylparaben, glutaraldehyde and ethyl alcohol.

Examples of fragrances can be aldehydes, ketones, or oils obtained by extraction of natural substances or synthetically produced as described above. Often, fragrances are accompanied by auxiliary materials, such as fixatives, extenders, stabilizers and solvents.

Examples of biocides include antimicrobials, bactericides, fungicides, algaecides, mildicides, disinfectants, antiseptics, and insecticides.

The amount of other optional ingredients effective for achieving the desired property provided by such ingredients can be readily determined by one skilled in the art.

Another aspect of the present disclosure is a personal care kit of parts, comprising the foamable personal care composition according to the present disclosure, wherein the cosmetically acceptable acidic component and the alkali metal carbonate or bicarbonate component are separated in different parts and do not contact with each other. In one embodiment, the alkali metal carbonate or bicarbonate component is dissolve in the carrier component comprising water and combines to one part.

Another aspect is a foamed product produced by mixing the components of the foamable personal care or the kit of parts according to the present disclosure. Preferably, the foamed product is in the form of a shampoo, a rinse-off conditioner, a leave-in conditioner, or a body wash.

The two reactive components can be dispensed from physically separate packages or from a unitary package with chambers in the kit of parts. The components of either type of packages can be applied simultaneously or substantially simultaneously to the skin or hair, or into a container, where they commingle and react. There may be two steps to applying the two reactive components. In the first step, one component with or without carrier component is applied to the skin or hair, or into the container, and in the second step, the other component with or without carrier component is applied over the first component within a period of time, such that commingling occurs when the second component is applied on top of the first component.

Preferably, the components of the system are dispensed from a unitary package. The package has at least two separate, non-communicating chambers for containing each of the different reactive components and an opening for dispensing the components. The opening of the chamber is designed to permit substantial simultaneous dispensing and commingling of the reactive components.

The form of the package can be a tube, a bottle, an aerosol or pressurized gas activated can or other suitable container. The unitary package may also have multiple chambers within, if there are more than two components. For example, a tube can be molded to have more than one partitioning wall inside to produce multiple chambers within the tube.

In use, the foamable personal care composition is applied to hair or skin. In one embodiment, applying the present foamable personal care composition constitute a method of conditioning skin or hair. In another embodiment, the method further comprises a step of messaging the hair or skin for from about 0.5 to about 10 min after applying the composition.

The following examples are intended to assist one skilled in the art to better understand and practice the present disclosure. The scope of the present disclosure is not limited by the examples but is defined in the appended claims. All parts and percentages are based on weight unless otherwise stated.

EXAMPLES

| Material | Trade name | Supplier |
|---|---|---|
| Sodium laureth sulfate | Texapon N 70 | BASF |
| Cocamidopropyl betaine | Tego Betain F 50 | Evonik |
| Cocoglucoside | Plantacare 818 UP | BASF |
| Disodium cocoamphodiacetate | Rewoteric AM 2 C NM | Evonik |
| Cetrimonium chloride | Dehyquart A CA | BASF |
| Xanthan gum | Xanthan FN | Jungbunzlauer Ladenburg |
| Hydroxyethyl cellulose 1 | Tylose H 100000 YP2 | Clariant |
| Hydroxyethyl cellulose 2 | Natrosol 250 HR | Aqualon |
| Carbomer | Carbopol 980 | Lubrizol |
| Cetearyl alcohol | Nafol 1618H | Sasol |
| Cellulose gum (carboxymethyl cellulose) | Cekol 2000 | CPKelco |
| Hydroxypropyl methylcellulose | Methocel K100M Premium | Dow Chemical |

As measured by a Brookfield RVDV II+ viscometer using spindle No. 4 at a rotation speed of 20 $min^{-1}$ at 20° C., the hydroxyethyl cellulose 1, hydroxyethyl cellulose 2, cellulose gum and hydroxypropyl methylcellulose exhibited viscosity of 5,630, 1,170, 620, and 3,840 mPa·s, respectively in 1% by weight aqueous solution of cellulose, respectively.

The foams to be tested were prepared by the method as follows. In a 100 mL glass breaker with scales, the foam of each composition was produced by adding 0.4 g citric acid powder into 10 g aqueous solution containing sodium bicarbonate, surfactant and thickener prepared from the compositions of E1 to E4 and CE1 to CE10 as shown in Table 1 respectively, and then manually mixing the mixture to homogeneity using a glass bar.

After the foams reached the highest volume, the volume was recorded as "the initial volume", and the time recording was started. At 15 minutes after the foams had the highest amount, the volume was recorded again as "the volume after 15 min". The ratio of the latter volume to the total volume of the foamable personal care composition was calculated by dividing "the volume after 15 min" by the volume of the foamable personal care composition (10 mL). All volume values were measured at 25° C. and under atmospheric pressure. The results are shown in Table 2 as below.

TABLE 1

Formulations of the foamable personal care compositions (except for the acidic component)

| Component | E1 (wt %) | E2 (wt %) | E3 (wt %) | E4 (wt %) | CE1 (wt %) | CE2 (wt %) | CE3 (wt %) | CE4 (wt %) | CE5 (wt %) | CE6 (wt %) | CE7 (wt %) | CE8 (wt %) | CE9 (wt %) | CE10 (wt %) |
|---|---|---|---|---|---|---|---|---|---|---|---|---|---|---|
| Sodium bicarbonate | 4 | 4 | 4 | 4 | 4 | 4 | 4 | 4 | 4 | 4 | 4 | 4 | 4 | 4 |
| Xanthan gum | | | | | | | | | 1 | | | | | |
| Hydroxyethyl | 1 | | 1 | 1 | 1 | 1 | 1 | 1 | | | | 0.5 | 2 | 1 |

TABLE 1-continued

Formulations of the foamable personal care compositions (except for the acidic component)

| Component | E1 (wt %) | E2 (wt %) | E3 (wt %) | E4 (wt %) | CE1 (wt %) | CE2 (wt %) | CE3 (wt %) | CE4 (wt %) | CE5 (wt %) | CE6 (wt %) | CE7 (wt %) | CE8 (wt %) | CE9 (wt %) | CE10 (wt %) |
|---|---|---|---|---|---|---|---|---|---|---|---|---|---|---|
| cellulose 1 | | | | | | | | | | | | | | |
| Carbomer | | | | | | | | | | 1 | | | | |
| Hydroxyethyl cellulose 2 | | 1 | | 1 | | | | | | | | | | |
| Cellulose gum | | | | | | | | | | | 3 | | | |
| Hydroxypropyl methylcellulose | | | 3 | | | | | | | | | | | |
| Sodium laureth sulfate | | | | | 3 | | | | | | | | | |
| Cocamidopropyl betaine | | | | | | 3 | | | | | | 3 | | |
| Cocoglucoside | | | | | | | 3 | | | | | | | |
| Disodium cocoamphodiacetate | 3 | 3 | 3 | 5 | | | | | | 3 | 3 | 3 | 3 | 1 |
| Cetrimonium chloride | | | | | | | | 3 | | | | | | |
| Deionized water | to 100% | to 100% | to 100% | to 100% | to 100% | to 100% | to 100% | to 100% | to 100% | to 100% | to 100% | to 100% | to 100% | to 100% |

TABLE 2

The results of the volume and stability of the foamable personal care compositions

| Result | E1 | E2 | E3 | E4 | CE1 | CE2 | CE3 | CE4 | CE5 | CE6 | CE7 | CE8 | CE9 | CE10 |
|---|---|---|---|---|---|---|---|---|---|---|---|---|---|---|
| Initial volume (mL) | 70 | 60 | 70 | 60 | 60 | 60 | 60 | 60 | 60 | 60 | 55 | 65 | 35 | 55 |
| Volume after 15 min (mL) | 35 | 32 | 40 | 45 | 20 | 20 | 20 | 20 | 25 | 28 | 20 | 25 | 30 | 35 |
| Initial volume/composition volume | 7 | 6 | 7 | 6 | 6 | 6 | 6 | 6 | 6 | 6 | 5.5 | 6.5 | 3.5 | 5.5 |
| Volume after 15 min/composition volume | 3.5 | 3.2 | 4 | 4.5 | 2 | 2 | 2 | 2 | 2.5 | 2.8 | 2 | 2.5 | 3 | 3.5 |

Figure 2:
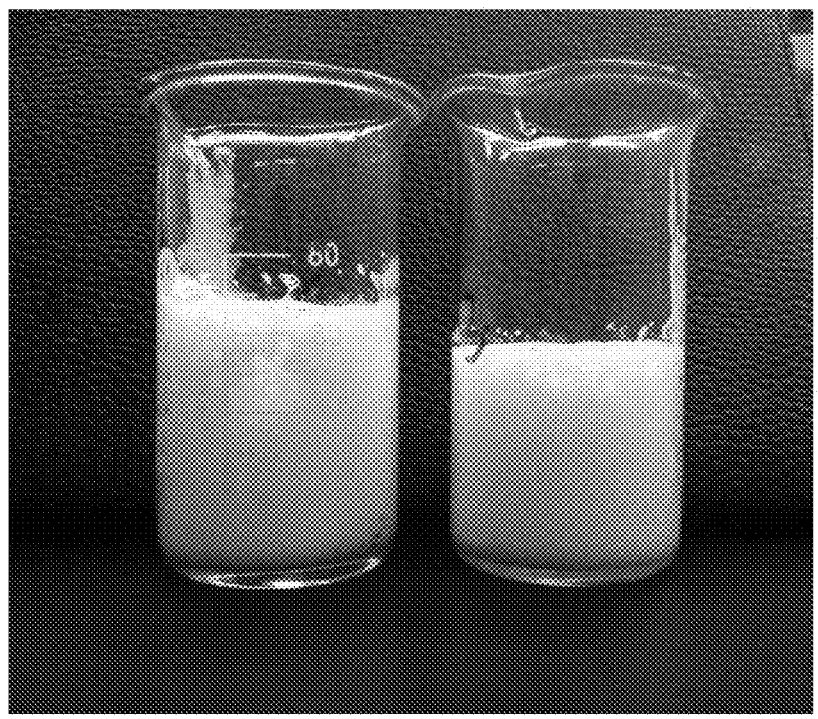
Figure 3:
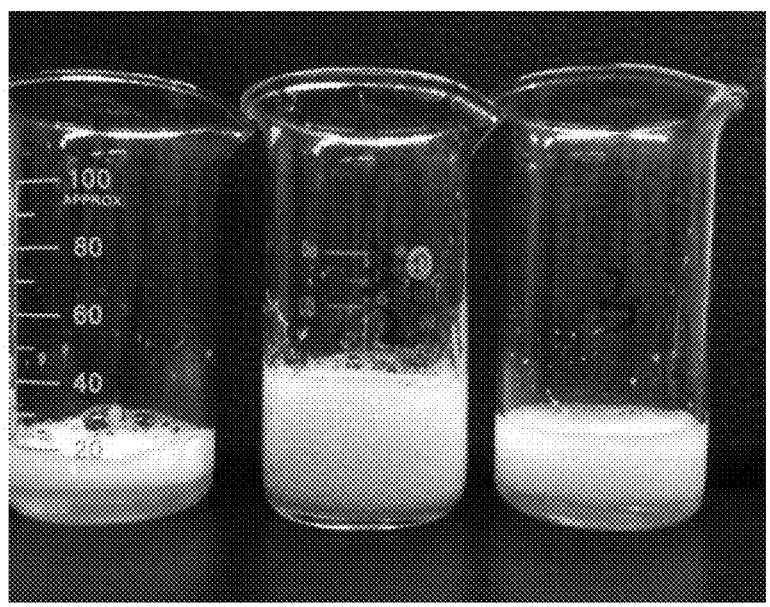
FIG. 3 illustrates the foams after 15 min of Comparative Examples 7, 8 and Inventive Example

As can be seen in Tables 1 and 2, the initial volumes and volumes after 15 min of the foams produced from E1 to E4 and CE5 to CE7 demonstrated that among different types of thickeners used in the examples, the celluloses having a suitable viscosity range exhibited larger initial volumes and better stability than those produced by other thickeners commonly used in the art, including cellulose having lower viscosity, xanthan gum and carbomer. All of the inventive examples surprisingly produced foams having an initial volume of no less than 60 mL, and a volume after 15 min of larger than 30 mL. Compared to E1 and CE8 to CE9, it demonstrated that the lower or higher amount of the cellulose deteriorated the stability of the foams. Moreover, as shown in FIGS. 1 to 3, it demonstrated that the viscosity and amount of cellulose used in the compositions were important for the initial volume and stability of foams.

Figure 4:
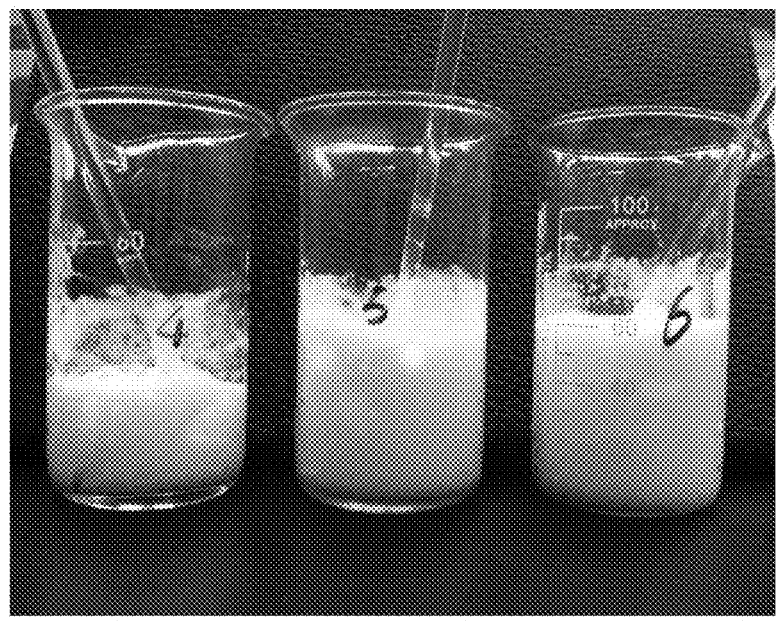
FIG. 4 illustrates the initial foams of Comparative Examples 9, 10 and Inventive Example 4.
Figure 5:
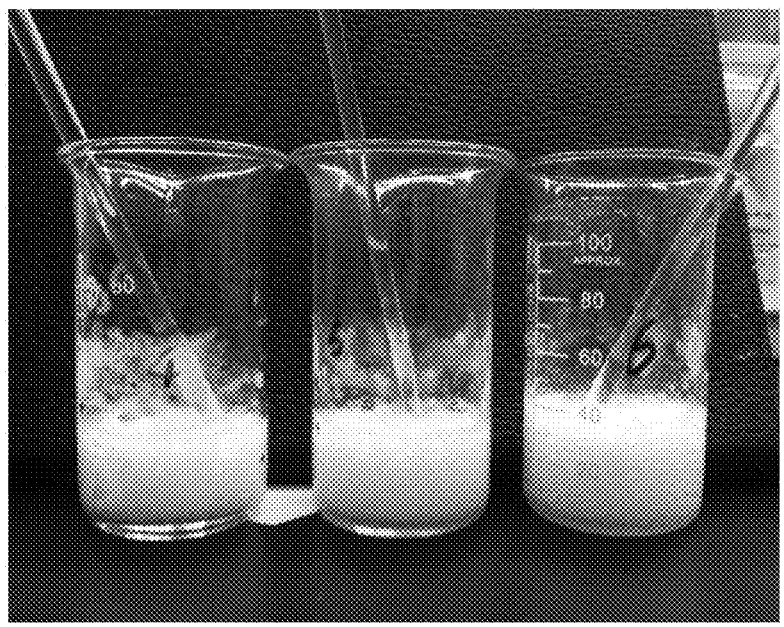
FIG. 5 illustrates the foams after 15 min of Comparative Examples 9, 10 and Inventive Example 4.

In addition, the initial volume and the volume after 15 min of the foams produced from E1 and CE1 to CE4 demonstrated that among different types of surfactants used in the examples, the amphodiacetates exhibited a larger initial volume and larger volume after 15 min than those produced by those well known in the art, for example, alkyl sulfates, betaines and monoalkyl quaternary ammonium salt. Compared to E1, E4 and CE10, it was also clear that the excessively low amount of surfactant would result in a poor initial volume. As shown in FIGS. 4 and 5, the suitable amounts of cellulose and surfactant have large influence on the initial volume and stability of foams.

These and other modifications and variations of the present disclosure may be practiced by those of ordinary skill in the art, without departing from the spirit and scope of the present disclosure. In addition, it should be understood that aspects of the various embodiments may be interchanged both in whole or in component. Furthermore, those of ordinary skill in the art will appreciate that the foregoing description is by way of example only, and is not intended to limit the present disclosure so further described in such appended claims.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A foamable personal care composition, comprising components:

(a) from about 1 to about 8% by weight of a cosmetically acceptable acidic component,
(b) from about 1 to about 8% by weight of an alkali metal carbonate or bicarbonate component,
(c) a carrier component, comprising:
(c1) from about 1 to about 4% by weight of a cellulose thickener having a Brookfield viscosity of from about 1,170 to about 5,630 mPa·s, measured by a Brookfield RVDV II+ viscometer using spindle No. 4 at a rotation speed of 20 $min^{-1}$ in 1% by weight aqueous solution of the cellulose thickener at 20° C.,
(c2) from about 3 to about 5% by weight of disodium cocoamphodiacetate, wherein a ratio of the disodium cocoamphodiacetate to the cellulose thickener is from about 2.5:1 to about 3:1, and
(c3) from about 80 to about 95% by weight of water,
in which the weight ratios of the components are based on the total amount of all components of the foamable personal care composition.

2. The foamable personal care composition according to claim 1, wherein the cosmetically acceptable acidic component comprises a cosmetically acceptable acidic compound selected from the group of a cosmetically acceptable organic acid, acidic salt thereof, a cosmetically acceptable inorganic acid, acidic salt thereof, and combination thereof.

3. The foamable personal care composition according to claim 2, wherein the cosmetically acceptable organic acid is citric acid.

4. The foamable personal care composition according to claim 2, wherein the acidic salt of the cosmetically acceptable organic acid is selected from the group of potassium tartrate, potassium bitartrate, calcium lactate, and combination thereof.

5. The foamable personal care composition according to claim 2, wherein the cosmetically acceptable inorganic acid is selected from the group of pyrophosphoric acid, phosphoric acid, sulfuric acid, and combination thereof.

6. The foamable personal care composition according to claim 2, wherein the acidic salt of the cosmetically acceptable inorganic acid is selected from the group of calcium sulfate, calcium phosphate, sodium aluminum phosphate, sodium aluminum sulfate, monosodium phosphate, disodium pyrophosphate, and combination thereof.

7. The foamable personal care composition according to claim 1, wherein the cosmetically acceptable alkali metal carbonate or bicarbonate component is sodium or potassium carbonate or sodium or potassium bicarbonate.

8. The foamable personal care composition according to claim 1, wherein the cosmetically acceptable alkali metal carbonate or bicarbonate component is sodium bicarbonate.

9. A personal care kit of parts, comprising the foamable personal care composition according to claim 1, wherein the cosmetically acceptable acidic component and the alkali metal carbonate or bicarbonate component are separated in different parts and do not contact with each other.

10. A foamed product produced by mixing the components of the foamable personal care composition according to claim 1 or the kit of parts according to claim 9.

11. The foamable personal care composition of claim 1, wherein the foamable personal care composition is in the form of a shampoo, a rinse-off conditioner, a leave-in conditioner, or a body wash.

12. The foamable personal care composition of claim 1, wherein the cellulose thickener is selected from the group of hydroxyethyl cellulose, hydroxypropyl methylcellulose, and combinations thereof.

13. The foamable personal care composition of claim 12, wherein the cellulose thickener is hydroxyethyl cellulose.

* * * * *